US006942962B1

(12) United States Patent
Pacocha (10) Patent No.: US 6,942,962 B1
(45) Date of Patent: Sep. 13, 2005

(54) COMPUTER MONITORING AND CONTROL OF FERMENTATION

(76) Inventor: Benedict George Pacocha, 333 N. Oakley Blvd. #3SE, Chicago, IL (US) 60612

(*) Notice: Subject to any disclaimer, the term of this patent is extended or adjusted under 35 U.S.C. 154(b) by 0 days.

(21) Appl. No.: 09/515,748

(22) Filed: Feb. 29, 2000

Related U.S. Application Data

(60) Provisional application No. 60/124,200, filed on Mar. 15, 1999.

(51) Int. Cl.[7] .............................. C12Q 3/00; C12Q 1/00; C12M 1/00
(52) U.S. Cl. ............................... 435/3; 435/4; 435/283.1
(58) Field of Search ............................... 435/3, 4, 283.1

(56) References Cited

U.S. PATENT DOCUMENTS 3,769,175 A * 10/1973 Berdelle-Hilge ......... 435/297.1
4,557,186 A * 12/1985 Brown ..................... 435/289.1
4,959,228 A * 9/1990 Skrgatic et al. ............... 426/11
5,900,547 A * 5/1999 Bartkiewicz ................. 73/447
6,150,133 A * 11/2000 Mead et al. ............. 435/252.3

* cited by examiner

Primary Examiner—Louise N. Leary (57) ABSTRACT

It is desirable to enhance reproducibility and control of batch fermentation processes. Some examples of these processes include: alcoholic beverage manufacture, and acetone and pharmaceutical production. A cellular yield curve defines the relationship between substrate utilization and cellular growth. The cellular yield curve is be used to create a mass balance between all of the reacting chemical species. This mass balance methodology is utilized to monitor the course of the reaction. The accurate description of the fermentation that is produced can facilitate reproducibility. Also, careful tracking of the course of the reaction can enable precisely timed interventions that will have an effect on the final outcome.

5 Claims, 10 Drawing Sheets

| Time During Fermentation | Yield (g cells/ g sugar) | Ammonia Needed (grams) | Water Produced (grams) | CO₂ Produced (liters) | Yeast Produced (C₆H₁₀O₃N) (grams dry wt.) | Ethanol Produced (C₂H₆O) (grams)* |
|---|---|---|---|---|---|---|
| 1st 3rd | .15 | 18.70 | 5.1 | 22.51 | 15.04 | 41.19 |
| 2nd 3rd | .052 | .65 | 1.79 | 25.54 | 5.20 | 47.68 |
| 3rd 3rd | .023 | .29 | .79 | 26.44 | 2.30 | 49.61 |
| Overall | .05 | .626 | 1.72 | 25.60 | 5.00 | 48.52 |

FIG.4

$$CO_2 \text{ solubility (in l } CO_2/l\, H_2O) =$$
$$-1.06556266071 \times \ln(°F) + 5.38424482284$$

FIG.5

$$\frac{\text{Change in yeast mass}}{\text{Change in time}} = \frac{\Delta X}{\Delta t} = \mu \times X$$

$$\ln\left[\frac{X}{X^{\circ}}\right] = \mu \times (t - t_{lag})$$

FIG.6

$$t_d = \frac{\ln(2)}{\mu}$$

FIG.7

$$\text{Ratio}\left[\frac{\text{l CO}_2}{\text{g sugar}}\right] = 0.271599039164 - (0.310674946821 \times \text{Yield})$$

FIG.8

Specific Gravity =
$(3.65201035996 \times 10^{-4}) \times S + 0.999953627005$

FIG.9

$$Y = \frac{\Delta X}{\Delta S}$$

FIG.10

$$\left[\frac{\Delta X \, (\textit{for decay})}{\Delta \textit{time}}\right] = b \times X$$

FIG.11

$$Y = \left[\frac{\Delta X}{\Delta S}\right] = \left[\frac{5.14794}{24.644}\right] = 0.20889 \frac{gX}{gS}$$

FIG.12

Xchrgd = 0.504076447609 ×
EXP(- 0.0816252748703 × Ratio)

FIG.13

| Sample Name | Time (hours) | X weight (grams) | S.G. Reading (g S/l, see EQSG) | Measured CO2 Flow (ml / min) |
|---|---|---|---|---|
| $t_0$ | 0 | 1.415 | 183.59 | 0 |
| $t_1$ | 15.75 | 2.73 | 178.11 | 3.944 |
| $t_2$ | 21.03 | 5.1 | 158.94 | 12.344 |
| $t_3$ | 24.5 | 6.18 | 147.99 | 15.074 |
| $t_4$ | 44.08 | 8.38 | 95.965 | 7.234 |

FIG.14

| A Interval | B Observed New X | C Total hours of interval | D Mass lost from starting X decay |
|---|---|---|---|
| $t_0 - t_1$ | 1.315 | 15.75 | 0.089145 |
| $t_1 - t_2$ | 2.37 | 5.28 | 0.0576576 |
| $t_2 - t_3$ | 1.08 | 3.2 | 0.06528 |
| $t_3 - t_4$ | 2.2 | 19.58 | 0.4840176 |

| A Interval | E Sub-total new mass (B + D) | F Ratio new X/Start X (Starting X + E) / Starting X | G Charge what new mass b? (EQXchrgd) |
|---|---|---|---|
| $t_0 - t_1$ | 1.404145 | 1.9923 | 0.471 |
| $t_1 - t_2$ | 2.4276576 | 1.88925 | 0.475 |
| $t_2 - t_3$ | 1.14528 | 1.22457 | 0.5 |
| $t_3 - t_4$ | 2.6840176 | 1.434307 | 0.493 |

| A Interval | H Decay of new mass (E x G x C x .004) | I Total new mass yield (E + H) | Amount of sugar used (g/l) |
|---|---|---|---|
| $t_0 - t_1$ | 0.0416652 | 1.4458102 | 5.48 |
| $t_1 - t_2$ | 0.024354261 | 2.45201186 | 19.17 |
| $t_2 - t_3$ | 0.007329792 | 1.152609792 | 10.95 |
| $t_3 - t_4$ | 0.103634643 | 2.7876522 | 52.025 |

| A Interval | J Average % S consumed | K Yield g X / g S | L Yield (fm curve) g X / g S |
|---|---|---|---|
| $t_0 - t_1$ | 1.4925 | 0.263833977 | 0.258098264 |
| $t_1 - t_2$ | 8.206 | 0.127908809 | 0.144275124 |
| $t_2 - t_3$ | 16.409 | 0.105261168 | 0.097997972 |
| $t_3 - t_4$ | 33.56 | 0.053582936 | 0.05021553 |

| A Interval | M % of actual Yield |
|---|---|
| $t_0 - t_1$ | 97.83% |
| $t_1 - t_2$ | 112.80% |
| $t_2 - t_3$ | 93.10% |
| $t_3 - t_4$ | 93.72% |

FIG.15

$Y = \{-6.67814305038 \times 10^{-2} \times [\ln(\%used)]\} + 0.284841059276$

FIG.16

| Interval | % fraction of S | Yield fm EQ%used | Ratio fm EQYld (l $CO_2$/g X) |
|---|---|---|---|
| $t_0 - t_1$ | 1.4925 | 0.2580973 | 0.79324921 |
| $t_1 - t_2$ | 8.206 | 0.14427497 | 1.52663404 |
| $t_2 - t_3$ | 16.409 | 0.097998 | 2.3594534 |
| $t_3 - t_4$ | 33.56 | 0.0502161 | 5.00801093 |

| Interval | Total new X (grams) | liters $CO_2$ predicted fm model (g X x Ratio) | liters $CO_2$ predicted by actual Yield |
|---|---|---|---|
| $t_0 - t_1$ | 1.445803 | 1.1469 | 1.1192 |
| $t_1 - t_2$ | 2.452006 | 3.7433 | 4.2872 |
| $t_2 - t_3$ | 1.1526299 | 2.71968 | 2.5095 |
| $t_3 - t_4$ | 2.787623 | 13.9604 | 12.9849 |

| Interval | Average measured $CO_2$ (ml / min) | liters $CO_2$ predicted fm avg of measured $CO_2$ flow rate at this interval | |
|---|---|---|---|
| $t_0 - t_1$ | 1.972 | 1.8635 | |
| $t_1 - t_2$ | 8.144 | 2.58 | |
| $t_2 - t_3$ | 13.709 | 2.6321 | |
| $t_3 - t_4$ | 11.154 | 13.1037 | |

FIG.17

COMPUTER MONITORING AND CONTROL OF FERMENTATION

This application claims benefit of Provisional No. 60/124,200 filed Mar. 15, 1999.

CROSS-REFERENCE TO RELATED APPLICATIONS

References Cited:
U.S. Pat. No. 4,856,421 Aug. 15, 1989 Whitford 99/276

STATEMENT REGARDING FEDERALLY SPONSORED RESEARCH OR DEVELOPMENT

Not Applicable (Self funded)

REFERENCE TO A MICROFICHE APPENDIX

Not Applicable (None submitted)

BACKGROUND OF THE INVENTION

The mass balance is one of the primary tools of engineering. Careful tracking of the materials consumed and produced enables one to adequately design for a process.

A simple example of a chemical mass balance would be hydrogen and oxygen combining to form water ($H_2O$). From the chemical formula of water, it can be predicted that two moles of hydrogen are needed for every one mole of oxygen used in the reaction. Any more than two moles of hydrogen would result in an excess of hydrogen. Any less than two moles of hydrogen would result in an excess of oxygen. At the end of the process, the amount of water formed can be observed, and an accurate measurement of the reactants used (hydrogen and oxygen) could then be determined.

Because mass cannot be created or destroyed, the mass at the beginning must be equal to the mass at the end. The exercise of modeling what happens to the mass through the course of the reaction is called a mass balance.

The process outlined in this patent involves a mass balance on the reactants through the course of a batch fermentation. The complicating feature of a batch fermentation is that the food that is used by the yeast (or other microorganisms) is not homogeneous. The yeast utilize the best food first. The 'best' food is described as the fraction of the total that yields the most new yeast mass.

The yield of the yeast mass from the food can be plotted as a function of time (or food fraction). This yield curve usually shows that yeast can turn carbon from the food into more yeast mass with a 30% efficiency at first. (0.3 of the food weight ends up as yeast mass.) This percentage then gradually decreases over time as the food fraction becomes more difficult to use.

This yield curve is the key to the mass balance of the fermentation. It can be employed in a dynamic fashion to show the progress of the fermentation. If the starting concentrations (reactants) are known, only the progress of one of the products need be monitored to complete the mass balance, and specify the concentrations of all of the chemical species in the entire reaction.

In this way, the course of a batch fermentation can be modeled from only a continuous carbon dioxide measurement. Measuring devices for the carbon dioxide evolution from the fermentation are called 'mass-flow' devices, and are available with various sensitivities and for various average flow rates. They can be acquired from scientific instrumentation catalogs such as Cole-Parmer™ and others.

The output signal from these mass-flow meters is analog, and must be converted to digital information for use by a computer. I am using a analog-to-digital converter card from a company called: Data Translation™. There are many other companies that offer similar devices.

The software for this application is being developed for the PC platform using the c++computer language. I am using Microsoft's™ Visual c++™ compiler, the industry standard at present.

The following details the modeling methodology for monitoring yeast growth from carbon dioxide ($CO_2$) evolution. It is important to note that this same approach can be utilized for batch processes in which alcohol is not the end product (such as acetone production). It begins with a description of how a batch of wort (sterilized malt sugars) is successfully inoculated with yeast. These yeast proceed to ferment the sugars in the solution, producing additional yeast mass, alcohol, and carbon dioxide.

Defining the relationship mathematically between the production of yeast, alcohol, and carbon dioxide as the batch progresses enables the prediction of the other species as long as one of them is measured. This relationship is outlined. Finally, the results of an experimental batch are compared to the predictions from the model. The results show this approach provides a valuable tool for routine monitoring and characterization of batch processes.

This invention relates to a process for monitoring, characterization, and control of batch fermentation processes. The production of alcoholic beverages, acetone, and many pharmaceuticals are examples of batch fermentation processes. Other inventions that utilize computer monitoring/control of fermentation processes involve attempting to keep one or two of the variables constant with a computer-controlled feed pump (e.g. U.S. Pat. No. 4,856,421). This is done in an attempt to make a batch process into a continuous-flow process. This approach is a 'mechanical' type of control. No attempt is made to describe the underlying chemical processes through mass balance calculations.

BRIEF SUMMARY OF THE INVENTION

The process outlined in this patent describes a mass-balance based methodology. This enables one to monitor all of the chemical species' concentrations during the course of the fermentation, without measuring all of them. For example, one can determine the level of completion of the fermentation by just the measurements of the carbon dioxide evolution. Since all of the chemical species' concentrations are monitored/documented, a 'fingerprint' of that particular batch can be kept for later scrutiny. This allows a greater degree of precision for increased reproducibility. Reproducibility is a much sought-after goal in many batch fermentation activities.

Monitoring of the chemical species during the course of the fermentation also allows one to affect a change in the conditions at just the right time. An example of this is found during the production of lager beer. During this type of fermentation, the temperature is lowered just as the yeast are starting a vigorous growth phase. The temperature must not be so low as to cause the yeast to go into dormancy. Precision monitoring of the course of the fermentation can facilitate this process.

The approach used involves first defining the groups of chemicals involved in the reaction. For example, all sugars are defined as $CH_2O$. These chemical groups are then carefully measured during the process. The yeast or bacteria will be able to increase their biomass from the food they consume in a certain way. The relationship (curve) of the yield of biomass with regard to the food consumed is defined. At that point, the entire reaction is defined. During the next fermentation, the production/consumption of the chemical groups can be dynamically monitored with just the measurement of one of the chemical species. The concentrations of the other species can be calculated, because the relationship between all of them has previously been defined.

DETAILED DESCRIPTION OF THE INVENTION

Yeast & Fermentation
Inoculum Preparation

As Pasteur discovered, microorganisms are constantly raining down on us at all times. Any container open to the air will soon be contaminated with microbe containing particles. Beer preparation is essentially the making of a growth media for yeast, and then setting conditions (i.e. temperatures) to regulate their growth. Yeast are but one of the millions of microorganisms that can take advantage of the rich growth media that is prepared (the wort). Some of the contaminant bacteria are even better suited for life in the beer wort in that they are able to reproduce up to 5 times faster than yeast. A normal value for the doubling time ($t_d$) for yeast during the period of fastest growth (exponential phase) is about 2–6 hours at room temperature.

Figure 1:
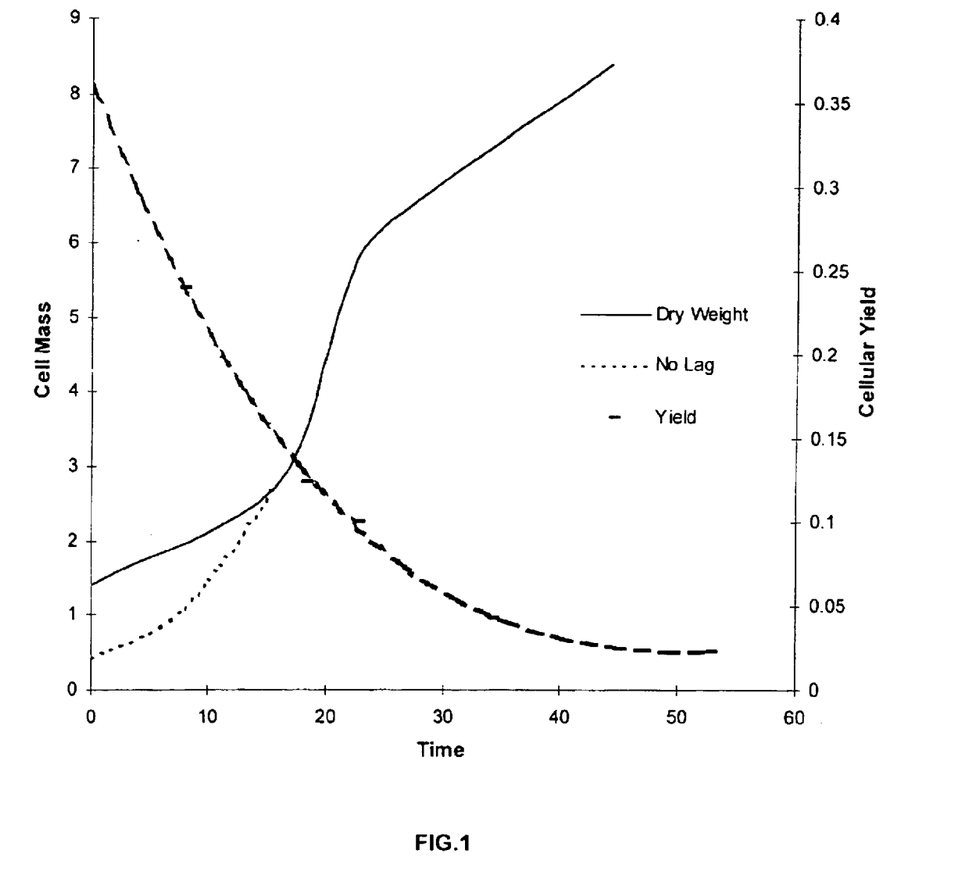
FIG. 1: This graph demonstrates that the cellular yield (cell mass created per gram of food) decreases as the fermentation progresses. The total cell mass (measured as dry weight) increases. The cells exhibit exponential growth during the first part of the process.

Once the yeast have established themselves in a particular batch, they have a strategy with which to keep many of the other microorganisms at bay. At the beginning of the batch, before any ethanol production, the yeast produce enough organic acids to acidify the pH to around 4. At this low pH (7 is neutral) very few other microorganisms are able to compete effectively with the yeast for survival. The contaminants are still present though, and a change in conditions after the fermentation is complete can give these bacteria the right environment to grow and produce off-flavors in the beer. Thus it is imperative that oxygen ($O_2$) is never allowed to contact the fermented beer, and that cold storage conditions be maintained. The goal of the initial inoculum (or yeast 'pitch') is to get the yeast fermentation underway quickly to exclude the possibility of off-flavors. The time between the initial inoculation of the wort and cell growth is called the lag phase. Referring to FIG. 1, the graph demonstrates and anaerobic yeast fermentation. The x-axis is time (in hours), the primary y-axis is the dry weight of cellular mass (in grams), and the secondary y-axis is the cellular yield (in grams cell weight divided by grams of sugar).

If the cells started fermentation immediately, the first visible signs of activity ($CO_2$ production) would lag behind as the wort absorbs $CO_2$ up to its solubility point There are two contributing factors to the lag time before active yeast growth in the fermentation.

1. One possibility is that the initial mass (1.4 grams/l in this case) contains 100% live yeast, but these yeast have either gone into dormancy for lack of food, or are conditioned to utilize a different substrate (type of food material). The wort is a mixture of different substrates, and the yeast will use the 'easiest' ones first. That is why a gram of food used early in the batch will yield more yeast than a gram of later-used food (see cellular yield curve). If the yeast are pitched from an older culture, they may have to 'retool' before they can start utilizing the new type of food that they are presented with. This illustrates the need to pitch active cells that are ready to utilize substrates.

2. Another factor that contributes to the lag phase is the possibility that there was really not much of a lag phase at all (see 'no lag' curve). The 'apparent' lag is there because the mass that was initially pitched in actuality contained very few active cells. (The balance being dead cells and other debris.) This small amount of inoculum might have been growing at the fastest rate all along, but it took awhile to 'break past' the initial starting debris mass. This is more likely for this particular batch. The inoculum for this batch was taken from an actively growing culture, but, as usual for malt extract, there are many grain particles in the media. Probably a very small percentage of the starting dry weight was active cells. This effect illustrates the need to pitch a high starting cell mass into the wort.

Both of these effects combine in varying proportions to result in the observed lag time.

Pitching Rates Breweries normally pitch at a rate of 1.5–2.5 g/l dry weight. At this rate each cell doubles between 2 and 3 times. This equates to about ¼th of the yeast produced from the previous batch. The brewmaster will crop a particular section of yeast from the fermentor cone. The lowest section might contain some debris and well flocculating (settling) yeast. These yeast tend to drop out of the solution before the fermentation is complete. The top section may contain yeast that poorly flocculate. These yeast tend to stay in the solution too long and cause clarification problems and excessive filter clogging. The center section of the yeast harvest is usually cropped, as it minimizes these extremes.

As mentioned before, these yeast's can be stored in a Cornelious™ keg under refrigeration until needed. The longer they are stored, or the more times the same culture is repitched, the more likely contamination will creep in. Starting a new culture from a commercial strain is discussed next.

Starting a Yeast Culture from a 'Smack Pack'

Many different high quality yeast strains are now available in 'smack packs' at most home brew shops. These contain a small bag of yeast within a larger bag of growth media. The bag is punched by hand to break open the inner bag into the surrounding growth media. This allows for a completely contained and aseptic beginning to the new culture. The bag begins to swell as the yeast metabolize the media into $CO_2$. This yeast needs to be pitched into freshly prepared media late in its' growth phase. This maximizes cell mass in addition to maintaining a high percentage of active cells. The active cell mass yielded by these packs is probably around 0.1–0.2 grams total, and is a pure, uncontaminated culture. Often this small amount of mass is used as an inoculum (or 'pitch') for an entire 5 gallon batch of home brew. This gives a cell concentration of the order of 0.005–0.01 g/l, and results in an unacceptable lag phase until the yeast builds enough mass to ferment the entire wort. A better method would be to create a small starter culture from the smack pack. If the smack pack was pitched into a ½ liter volume of sterilized wort and fermented, a final cell volume of around 4–5 grams total would be produced. This would result in a final pitching rate of 0.21–0.26 g/l into a 5 gallon batch of home-brew. This pitching rate, although not as high as the commercial breweries rate of 1.5–2.5 g/l, results in a minimal lag time (~10 hours). The pitching rate of 0.2 g/l is perfectly acceptable provided that most of the cell mass is active, and that conditions are highly aseptic.

The goal is to provide at least a 0.2 g/l active cell pitching rate to the freshly prepared beer wort. Yeast cell mass can be generated either without oxygen (anaerobic) or with oxygen (aerobic). With an anaerobic fermentation, much of the food sugar is converted to ethanol at the expense of cell mass. A usual cell/anaerobic yield is around 0.05 g cells/g sugar. With a wort of average gravity this gives around 8–9 g/l in 2 days.

Aerobically grown yeast have a better yield, as ethanol formation is partially subdued. A culture kept aerobic (with a shaker tray for example) normally yields 15–16 g/l in one day. When the aerobic and anaerobic cultures are compared with respect to the removal of the first 50% of the sugars, the aerobic culture is over 2 times faster and gives over 3 times the cell mass of the culture kept anaerobic. Overall cell 1 food yields for aerobic cultures are from 0.1–0.3 g cells/g sugar.

You may have read about aerobic yeast yields at 0.5 in the bread yeast industry. These yields are only possible with a fed batch system, and will not be realized with a simple batch culture. Some effects that turn on ethanol production (and hence affect the aerobic yeast yield) are:

1. glucose inhibition (Crabtree effect): an abundance of sugar causes ethanol production regardless of oxygen concentration.
2. oxygen limitation (Pasteur effect): any limitation of oxygen supply causes ethanol production.

It is difficult to keep up the oxygen concentration in a 2 liter shake flask. See FIG. 2 Referring to FIG. 2, the drawing shows a common 2 liter Fernbach shake flask. The small surface area on the top, and the foam that forms, limits oxygen transfer to the liquid. Arrow 1: the sponge cap. This allows the transfer of air but not contaminants. Arrow 2: the foam. Arrow 3: the wort or medium (substrate). Arrow 4: Agitators.

Figure 2:
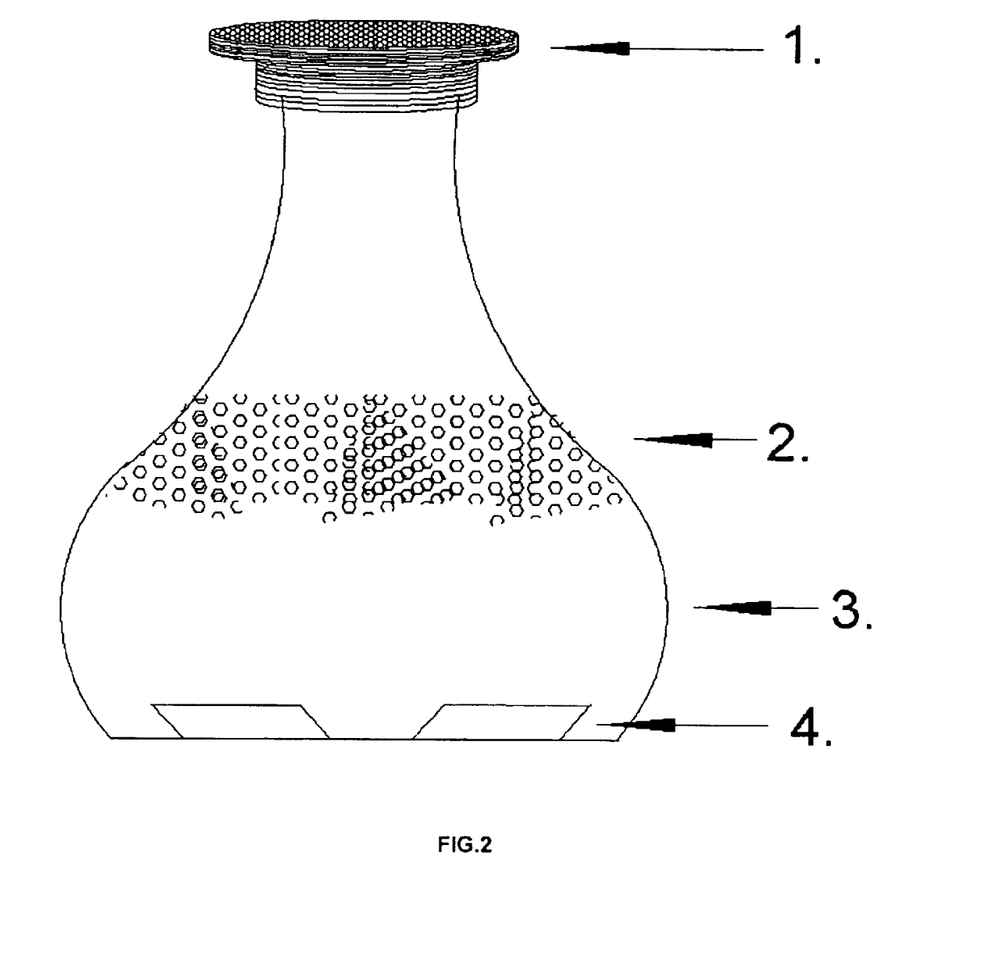
FIG. 2: This figure demonstrates the point that, unless shaken vigorously, little oxygen can be delivered to wort (growth media) while yeast are being cultured for a fermentation.

If the 2 liter flask is filled with 2 liters of wort, the surface area (on top) is reduced by the neck (decreasing the oxygen transfer area). The foam build up also serves as a barrier to oxygen transfer. All this lowers oxygen in the wort, increasing ethanol and decreasing cell mass. If 1.5 liters of wort are shaken at 200 RPM in the 2 liter Fernbach flasks, a cell dry weight of 15 grams/liter can be attained in one day. So, with 22.5 grams of cells per flask, multiplied by 3 flasks (3 is the maximum number that will fit on one large shaker tray-table) a total of 67.5 grams of cells (22.5×3) can be produced in 2–3 days (at room temperature). (The first 24–48 hours would be spent waiting for the smack pack to swell, the last 24 hours would be growth in the Fernbachs.) Thus, 3 flasks would provide a 0.2 grams/liter pitching rate for 90 gallons, or one flask per 30 gallons of wort. Again, this is on the low side, but will be fine as long as care is taken to prevent contamination.

Fernbach Media Preparation

Figure 9:
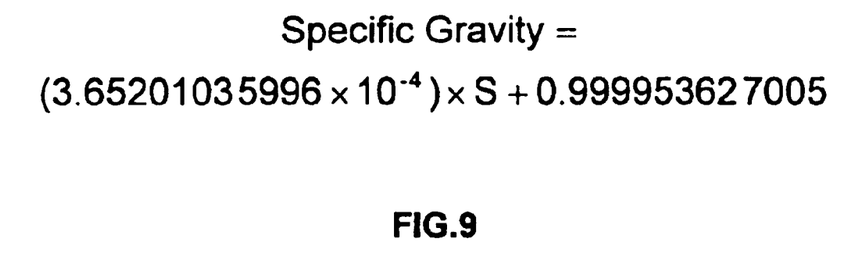
FIG. 9: The solution density for a fermentation medium is normally measured with an hydrometer. This reading (for a barley malt sugar solution) is easily converted to grams of sugar per liter using this equation.

As mentioned before, the smack packs are totally self-contained, and no contamination problems are posed until they are opened. The wort for the Fembachs must be prepared, sterilized (via autoclave/pressure cooker or boiling), and cooled to room temperature before the yeast from the pack is pitched. Dry powdered malt extract (available at home-brew stores) or some frozen wort from a previous brew is best used to formulate the wort. Dry malt extract is dissolved in water at between 0.33 lbs. (150 grams)/liter to 0.44 lbs. (200 grams/liter. 0.6 lbs. onto 1.5 liters in the Fernbach flask will give a starting specific gravity of ~1.067. (See EQSG, FIG. 9) You can dissolve the powder by setting the flask on the shaker for awhile. It is recommended that the pH be dropped to ~4 using food grade phosphoric acid. The pH will be low anyway (around 5 or so). This pH drop will mimic that which is attained in an anaerobic fermentation along with its anti-microbial effects. Hops also have anti-microbial properties and may be added. The Fernbach is then capped and the media is sterilized in an autoclave or pressure cooker. The sponge cap allows release of the gasses while preventing the entry of contaminants. Autoclaving/pressure cooking allows the media to be sterilized in the growth flasks. If the media is boiled, the shake flasks must also be sterilized (via boiling) as well. The media must then be transferred under sterile conditions, which is difficult without the proper equipment. Simply baking the shake flasks is not completely effective, as microorganism spores are very resistant to dry heat.

To avoid breakage, carefully cool the flasks to room temperature. Sterile technique must be used when pouring the contents of the pack into the wort.

Sterile Transfer Technique

Use a table that is sheltered from drafts and wipe it's surface with 200 proof alcohol. With clean hands, swab the yeast swollen yeast pack with alcohol and open. Take the flask, remove the cap, and briefly flame/heat the opening (with a flame from a Bunsen burner or propane torch). This gets the air from the bottle moving in an outward direction. Again, do not flame the flask long or the flask may break. Pour the contents of the pack into the flask, flame the flask again, and cap. Remember during this procedure that bacteria is falling down constantly like rain upon the table. Endeavor to keep the opening of the flask tilted (to reduce the surface area open to air from the top), and refrain from breathing when the media is exposed.

This is an example of the sterile transfer of a yeast culture. A transfer hood (eluded to earlier) pushes filtered air past the flask during this procedure which prevents contamination during transfers. These hoods are quite expensive, and their purchase is impractical for this application. If you have performed the transfer correctly, your yeast now find themselves in a rich media with no competition. Set the flask in the shaker and, in 24 hours, you should have 22–23 grams of yeast for pitching. Remember, the yeast should be used while in an active state. The freshly prepared wort (in the main fermentation vessel) must be ready to accept this yeast pitch after this 24 hour period has expired. Any increase in this timing will result in a longer lag time and possible off-flavors. A sterile transfer is again performed into the main fermentation vessel.

Fermentation Theory

Figure 3:
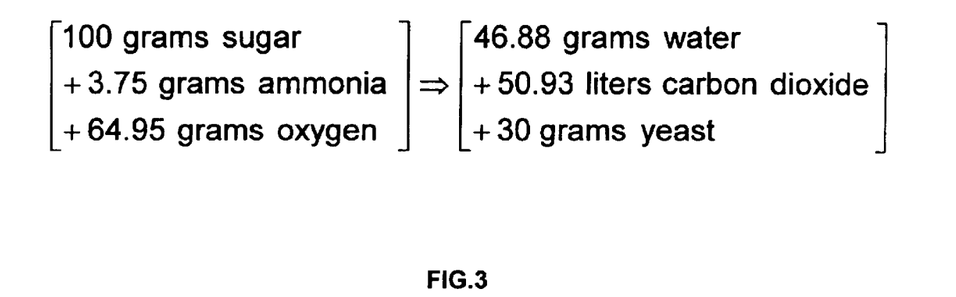
FIG. 3: This equation demonstrates how stoichometry can be used to quantify the chemical species during a fermentation.

As was stated before, it is desirable for the freshly prepared wort to be brought up to at least 10 mg/l oxygen before the yeast is pitched. This makes the yeast's new environment more accommodating; i.e. gives the yeast more energy to start an exponential growth phase. The quantity of new yeast that this oxygen can produce is strictly defined with stoichometry. See FIG. 3 FIG. 3 is a chemical balance for an aerobic yeast culture with a 0.3 gram cells/grams sugar yield.

From this equation it is calculated that, at an oxygen concentration of 10 mg/l, an extra ½ gram per barrel (31 gallons) of yeast is produced. The new mass gained is negligible; the oxygen is used by the yeast to 'retool' for the anaerobic fermentation at an accelerated rate.

Once the culture goes anaerobic, the quantities of the chemical species are again precisely defined by stoichiometry. At the beginning of the fermentation, the yields (in grams cells/grams sugar) are the highest. Another way to say this is that the yeast use the best (most productive) foods first. As the culture proceeds, the yield of cells per gram of substrate is reduced.

Figure 4:
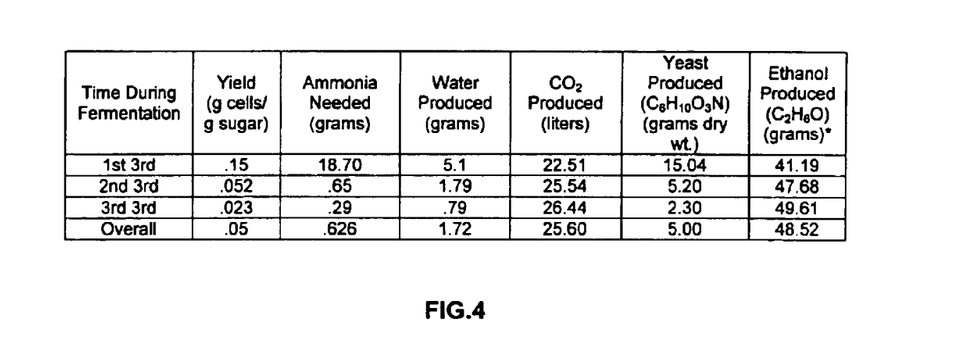
FIG. 4: This table demonstrates that the cellular yield is the key to quantifying the concentrations of all of the chemical species involved. A yield curve can be used to dynamically graph the progress of a fermentation.

FIG. 4 shows how the volumes of the different chemical species change during each third of the fermentation progression. The final line is for a yield of 0.05 g cells/g sugar; the overall reaction summed at the time the yeast is usually harvested (1 to 2 weeks). The quantities are based on the usage of 100 grams of substrate (sugar) at standard temperature and pressure. If ethanol volume is desired, divide its weight (in grams) by its density (0.789 grams/ml).

You can see that at any one point during the batch (or for a certain fraction of substrate), if the yield is known, the quantities of the other chemical species can be calculated. As each percentage point of the substrate is consumed, the yield can be calculated. A curve is then fitted to the percentage fraction of substrate vs yield data, and an assessment of yields can be made as the batch proceeds. The yield from the yield curve is correlated with a $CO_2$ vs yield curve to define how much sugar has disappeared. This information can then be used to predict the quantities of all of the reactants.

The solubility of $CO_2$ in the solution must be reached, however, before any is evolved. The solubility of $CO_2$ in water is related to the temperature and is defined by $EQCO_2sol$. See FIG. 5.

Figure 5:
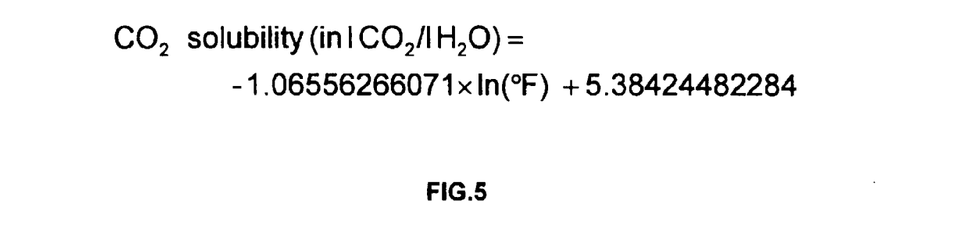
FIG. 5: The solubility of $CO_2$ in water is related to the temperature. For a given temperature, the $CO_2$ solubility can be estimated using this equation.

So, the $CO_2$ solubility at 73° F. would be $0.812/CO_2/l$ $H_2O$, and can be compensated for in the $CO_2$ volume measurement. This solubility has been calculated to comprise up to 2–4% of the total volume evolved from an average beer fermentation.

In summary, it was shown that from $CO_2$ evolution, and a yield curve describing the cellular yields at each substrate fraction, the formation of all of the materials in the batch can be described. The most important component to describe is the formation of yeast. It is the rate of yeast doubling that determines the speed of the fermentation. The speed of the fermentation is manipulated to produce the three major styles of beer: ale (fast), steam (medium), and lager (slow fermentation).

As the cells (represented herein as 'X') reproduce, their growth rate (represented as '$\mu$' or 'mew') can be calculated (EQ$\mu$). See FIG. 6

Figure 6:
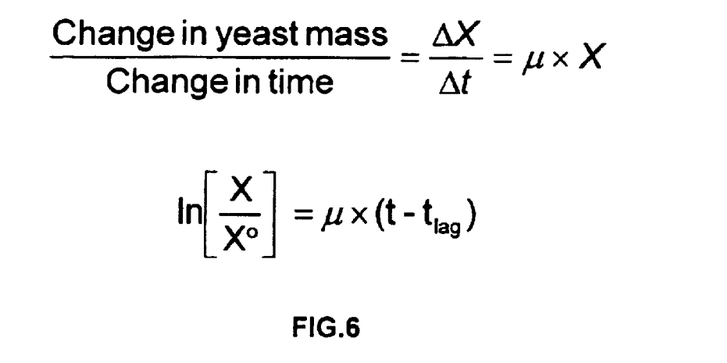
FIG. 6: The specific growth rate of cells is represented by the variable '$\mu$' (pronounced 'mew'). This equation shows how $\mu$ is calculated.

The change in yeast over time is described by EQ$\mu$. The natural log of the ratio between ending cell mass (X) and starting cell mass (X°) is equal to $\mu$(growth rate) multiplied by the time (subtracting out the period of no growth: lag time ($t_{lag}$)). From this calculation of $\mu$, the time at which the population doubles (or $t_d$) can be calculated (EQ$t_d$). See FIG. 7

Figure 7:
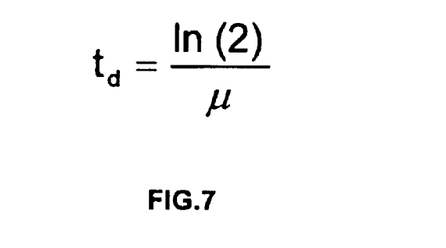
FIG. 7: This equation shows how use $\mu$ to calculate the amount of time it takes for a cell population to double.

This equation states that the doubling time of a population ($t_d$) is equal to the natural log of 2 (ln(2)) divided by the growth rate ($\mu$).

For each fermentation, a graph of the growth rate ($\mu$) and/or the doubling time ($t_d$) can serve as a 'fingerprint' for the course of the fermentation. The knowledge of these critical facets of the fermentation can enhance reproducibility. It is also interesting to compare (via fermentation characteristics) the different chemical species in mixtures when the constituents are altered. The fermentation characteristics are defined by:

1. The quantity and condition of the yeast that are initially pitched.
2. The components of the wort (or 'must' as it is called in wine making) e.g. different grains, fruits, etc.
3. The conditions that are set upon the reaction (e.g. temperature).

Wine fermentation is an example of an effect that the medium has on the fermentation. Wine 'must'(from freshly pressed grapes) is extremely high in sugars. The yeast growth is limited, however, by a severe limitation of nitrogen. This limitation sets a 'ceiling' to the level of yeast mass. The reaction must proceed with much less cell mass, so it is extended into a much longer process. This mass limitation can be seen/quantified in the reaction mass yield curve (See the section on: 'preparing a custom yield curve' later in the paper). As each fraction of the 'must' gets consumed it can be associated with a certain cell mass yield. When the nitrogen limitation is reached, the yield approaches zero, but there is still plenty of fermentable material present. That set amount of cell mass must then finish the job without creating more mass (without growing). Cells starved in this way will metabolize the sugars slowly, go into dormancy, and/or create energy storage polymers that they can hold on to in hope of some additional nutrient (in this case nitrogen) availing itself. This effect happens in beer wort too, but the effect is more dramatic in wine must where the limitation is more acute.

$CO_2$ Production vs Substrate Consumption

As shown earlier, the $CO_2$ production is strictly related to substrate (malt sugars) consumption via the yield (Δ cell mass/Δ substrate). The relationship is correlated with this regression line $EQCO_2$. See FIG. 8 This regression line is a linear fit, with $r^2=-0.99998985$.

Figure 8:
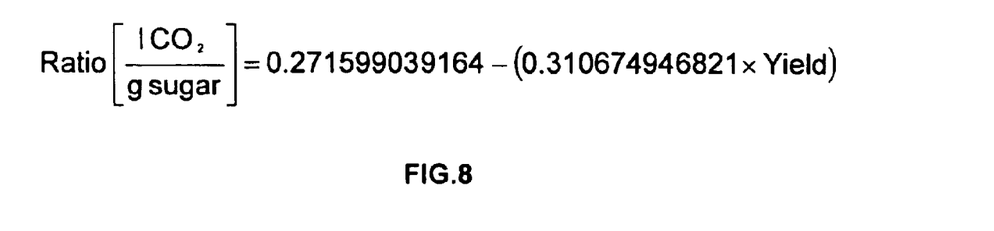
FIG. 8: There is a strict mass balance relationship between the $CO_2$ produced and the sugar consumed. This is a regression line describing this relationship for a given cellular yield.

The amount of sugar consumption can be calculated with $EQCO_2$ from the $CO_2$ volume (in liters) if the yield is known.

The yield curve (covered later) defines the yield for the average percentage fraction of the substrate. Each fraction of the substrate will have it's own specific yield value, and the highest yielding will be used first. Any $CO_2$ evolution volume is defined by and must be justified with the yield curve. It is through the yield curve that the $CO_2$ volumes can be made sense of, and the production of the particular chemical species tracked. Thus, for a particular interval, when the $CO_2$ volume is accumulated and a calculation is to be made, the yield used with $EQCO_2$ to get sugar mass consumed must equal the yield derived from the yield curve relating the percentage fraction of substrate to the yield (EQ % used; covered later). This is an iterative process. The answer is then logged and used as a reference for the next calculation. An example calculation is as follows:

Suppose we know that out of 100 g/l sugar, 10 g/l has already been consumed. Furthermore, we have to make a calculation and we have just measured a $CO_2$ production volume of 0.5 liters $CO_2$/l. We know that 10% of the sugars have been consumed, so we know that the value on the percent used curve (EQ % used) is going to be greater then 10.

The percent used curve (covered later) returns a yield value from an input of the average percentage fraction that was consumed over that interval. An example would be: if the first 10–20% of the substrate was consumed, the input to EQ % used would be 15 (the average of 10 and 20). The yield on that fraction would then be given.

Back to the original problem. The first step is to get a starter value from EQ % used. We know the value must be greater than 10, and we know that whatever it is, it will be the average of the percentage fractions used during that interval. Let's start with a value of 12. Say that for 12. EQ % used returns a yield value of .119 (9 cells g sugar). Using this yield in $EQCO_2$ gives a ratio(l $CO_2$/g s) value of 0.2346. At 0.5 liters $CO_2$, which is what we said we had measured, this equals 2.131 g sugar used. 2.131 g is the total amount of substrate (S) used. The value needed for EQ%used is the average of the fractions over that interval. So, the average of 10% (starting fraction) and 12.131% (ending fraction) is 11.0655 %. This 11.0655 value is then input into EQ % used again until the yield given by EQCO2 equals that predicted by EQ % used. Both equations have a yield (Y) value and a substrate (S) value that have to correspond. The best way to approach the answer is to start at the lowest EQ % used Y value (say 10.1 in this case), and keep trying higher ones until the substrate (S) grams are equal in both equations. This is called an iterative solution to a system of equations. At that time the yield value can be used to predict the accumulation of the different species. The grams of substrate (S) lost are added to that already consumed, and the new cell mass is added as appropriate to the ending cell mass of the last interval/measurement.

Beginning the Fermentation: 3 Inputs

To begin this process, only 3 simple input parameters will need to be logged into the program:

1. Starting Gravity The yield curve is keyed off of the percentage fraction of each substrate. The specific gravity (quickly measured with a hydrometer) will be converted into grams of sugar with EQSG (shown later). A logged reference at each interval will show the degree of attenuation (or percent destruction of sugars). Temperature program changes for the fermentation an be keyed off of the degree of attenuation. The final degree of attenuation for beer is usually between 73–77%.
2. Initial Cell Mass For the unit to accurately keep track of the cell mass accumulation, the starting cell mass must be known. The lower this number is the less significant. Each method of inoculum preparation will yield an approximately consistent cell mass, so the inoculum dry weight need only be taken once. Remember that dry weights are taken of washed cells dried at 100° C./212° F. (no dissolved sugars should be included). That cell mass is than divided by the total volume of the fermenter for the starting cell mass in g/l.
3. Starting Wort Volume A starting volume would allow for accurate presentation of the materials in g/l. This also will be consistent for a given pre-boil volume and boiling time.

Preparing a Custom Yield Curve

A yield curve describes how much cell mass can be derived from a particular food. As a batch culture proceeds, it preferentially uses substrates (food). The materials that are the highest yielding are used first. The substrate is normally measured by solution density with a hydrometer. This reading for beer wort (specific gravity or S.G.) usually starts at between 1.030 and 1.070. This measurement can be converted to grams of sugar (S) via EQSG. See FIG. 9 This equation is a regression line with $r^2=0.99999$; "S" is in grams/liter.

As each gram of sugar gets converted, it lowers the density of the solution. The grams of sugar consumed can be followed by the S.G. readings.

The S.G. of ethanol is 78.9% that of water, so this introduces a slight error. Considering that the final ethanol content of beer is usually 3–5%, and that the percentage is actually much lower through the course of the fermentation, the error introduced will impact the results in the 1–3% range. The S.G. reading issue should be revisited if fermenting worts of very high gravity such as wine.

Figure 10:
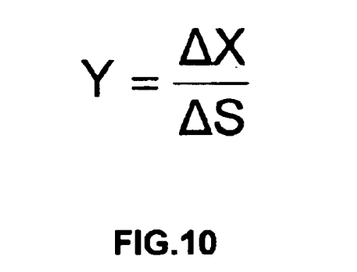
FIG. 10: This equation illustrates that the cellular yield equals the change in cell mass (X) divided by the change in substrate mass(S).

The yield is simply the change in cell mass (X) divided by the change in substrate (S). FIG. 10

There is one complicating factor though. Organisms have an energy (and hence substrate) cost to run their metabolisms. This is called endogenous decay (b), and is usually about 0.1/day or 0.004/hour. See FIG. 11

Figure 11:
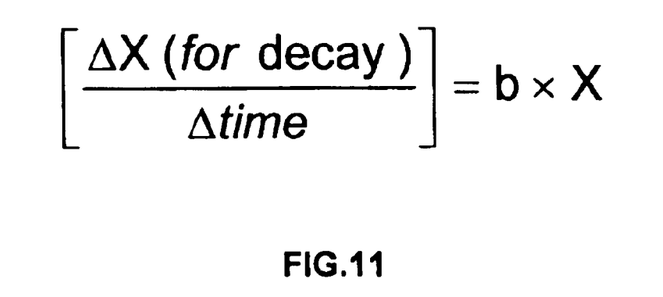
FIG. 11: This equation illustrates that there is a cost to the cells to run their metabolisms. This is called endogenous decay (b).

So, if you look at an interval with a starting X of 5 grams and in 5 hours the weight is 10 grams, your change in X (ΔX) is not 5 grams; it's a little more. The 5 original grams have spent 5 hours decaying/metabolizing, and a fraction of the new cell mass has also had to decay. It follows that the 5 original grams' mass after 5 hours would be expected to equal 4.9 grams. (0.004/hr×5 hrs=0.02; 5 g×0.02=0.1 g; 5 g−0.1 g=4.9) 47% of the new mass should be 'charged' for decay (See: 'Charging new X for Decay'), so: 5.1×0.47= 2.397 g; 2.397×(0.0041 hr×5 hrs)=0.04794 The new mass is than the observed new mass (5), plus the decay mass from the old mass (0.1), plus the decay mass from the new mass (0.04794). ΔX=5.14794 grams.

Figure 12:
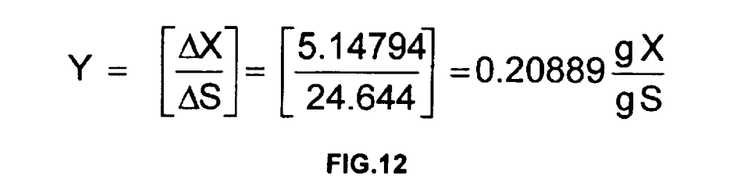
FIG. 12: This equation demonstrates a cellular yield calculation with actual (experimental) values.

You can see that the longer the interval length, the more important b becomes. For the sake of continuing the example, let us say that the S.G. during this 5 hours dropped from 1.058 to 1.049. The sugar concentration (in g/l) using EQSG goes from 158.944 to 134.299, or 24.644 grams used. Then the yield calculates as FIG. 12.

A yield curve is constructed by associating the location of that substrate consumed in the batch (as a % of the total) with the calculated yield value. This can take the form of one equation completely describing the substrate. This equation can be derived from a statistical analysis of the experimental data. Alternatively, the data can be used to create a look-up table for each substrate fraction. Either way, providing a known substrate fraction will then equate to a yield value for that fraction.

Charging Endogenous Decay Costs (b) to Newly Formed Cells

If the yeast cells' mass (X) increased linearly, then the new X charged for decay (b) during that interval would be ½ of the newly formed mass. Because yeast grow exponentially, this percentage will decrease as the ratio of ending X/starting X (X/X°) increases. This relationship is described by the following equation and graph (EQXchrgd). See FIG. 13 The percentage of X that should be charged for decay (y-axis) is plotted against the ratio of starting to ending X for that interval.

Figure 13:
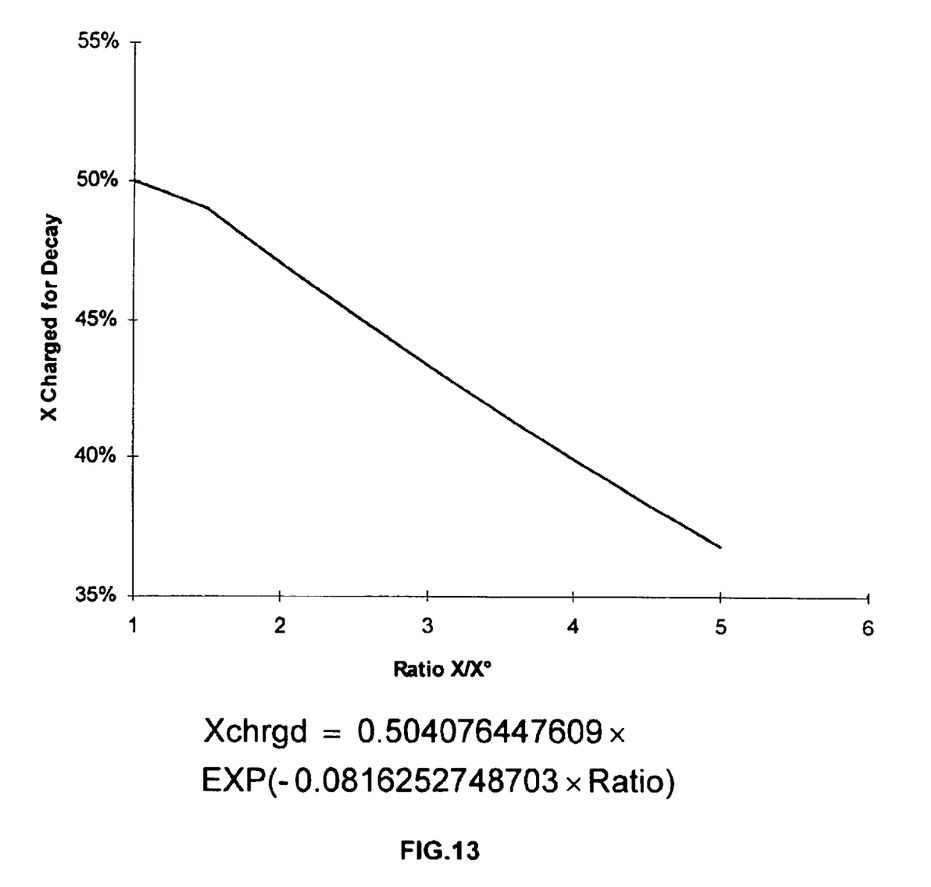
FIG. 13: This curve describes that the 'average' amount of new cells generated is not quite one half of the new cells. This is because cell growth is sometimes exponential, and not linear. This number depends on how much the cell mass has changed during the interval involved. Because the preferred embodiment of this invention will use measuring intervals shorter that the doubling time of the yeast, this problem will not come into play.

You see that at a X/X° ratio of 1.5, the X charged for decay should be 0.49. At a X/X° ratio of 4, X charged should be 0.4. Normally observed yeast doubling times are between 3–6 hours, so if interval lengths are kept at 1 hour (as planned), a 0.5 fraction of the new mass charged for b will be fine. (This amount of mass loss will be insignificant compared to the total mass.)

To continue our example, say our beginning S.G. of 1.058 was the start of the fermentation. So 158.944 g S/l is 100%. At 134.299 g/l, 15.5% of the total was consumed. The yield value we arrived at was an average over this interval, so let's associate that yield with the average percentage value (15.5%/2 or 7.7527%). Thus: when S % used=7.7527%; Yield was: 0.20889 g X/g S.

We have our first point for the yield curve. Continue to calculate these points for the remaining batch, and correlate a regression line to them. You will see that the yield starts a high on the initial substrates (~0.3), and approaches zero towards the end. You can see that the longer the interval length, the less accurate the curve will be. Sample points therefore should be on the same scale as that for which the curve will be used. A normal yield of 0.05 is used in the brewing industry because at the time when the yeast is usually harvested, the average of the many different yield values, combined with the decay time, yields around 5 grams of yeast for every 100 grams of sugar. Here are some data from a real test fermentation along with the yield curve calculations (as above) FIG. 14.

Figure 14:
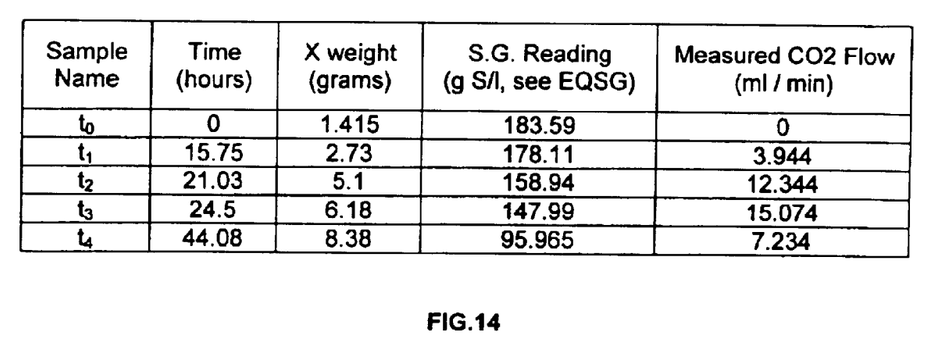
FIG. 14: This table contains data from the test fermentation that was used to validate this technique.
Figure 15:
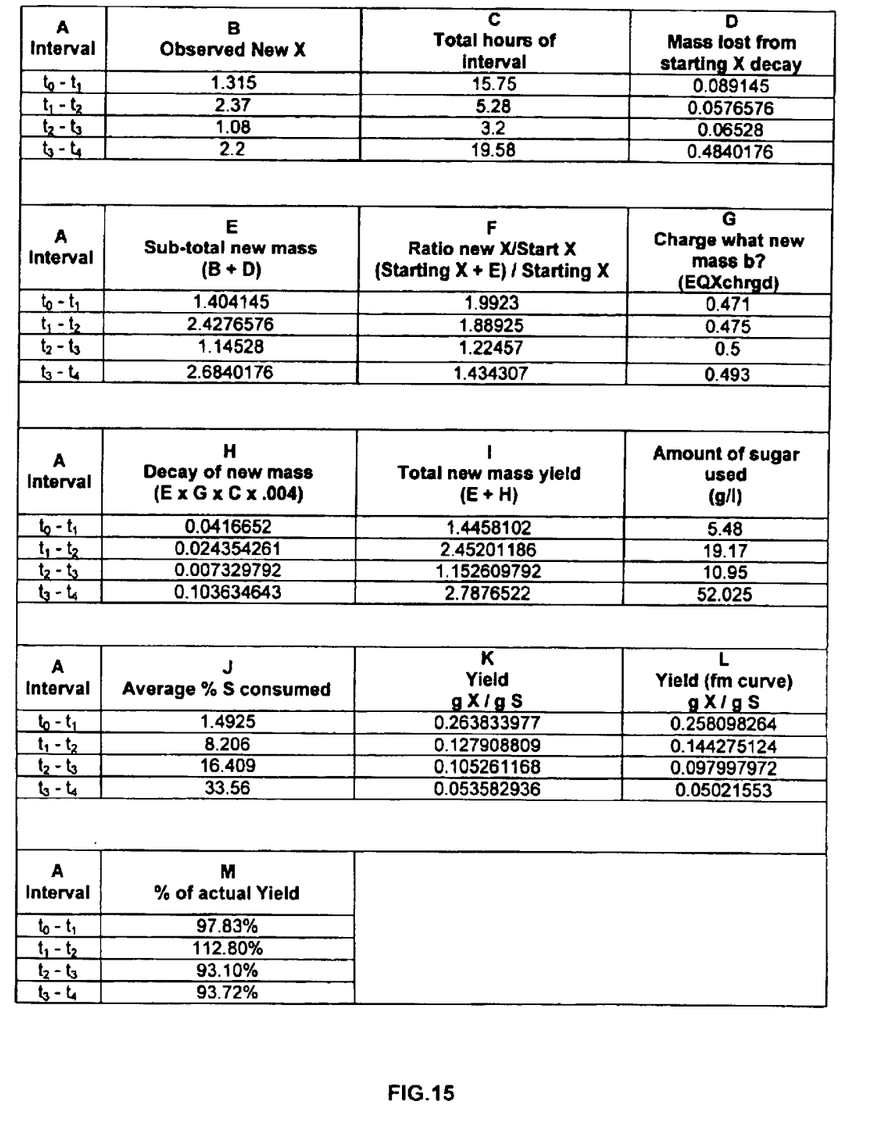
FIG. 15: This table demonstrates the calculations that are performed to develop the yield curve in FIG. 16.

The test fermentation data table documents the actual data acquired from the test fermentation. The value of b used was 0.004/hr. See FIG. 15

Figure 16:
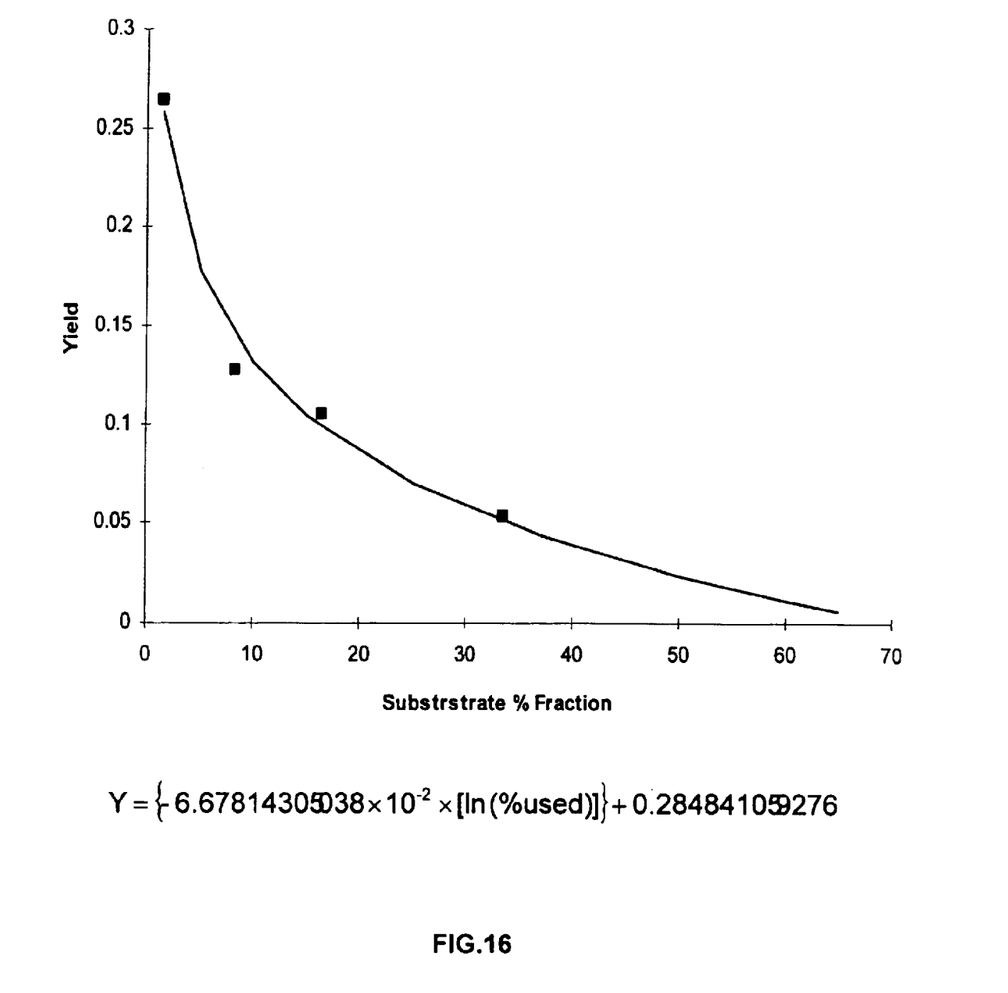
FIG. 16: The graph here depicts a yield curve that was fitted to the data points obtained from the test fermentation.

Referring to FIG. 16, this graph compares the four data points with the yield curve (EQ % used). The regression line is a log fit; $r^2$=−0.9924. If there were more then just 4 data points, the points would be tighter, and a higher correlation line could be determined (not that an $r^2$=−0.9924 is particularly bad). This yield curve allows one to predict the yield from the knowledge of the particular fraction of substrate that is being consumed. With analytical chemistry instruments, one could even find the particular chemicals associated with each fraction. The goal for this project is to describe the fermentation by $CO_2$ evolution. With a percentage fraction of S consumed (this is known from a correlation of $CO_2$ production volume with S loss) one can get a yield value which in turn defines the mass generation of all of the chemical species (cells, ethanol, $CO_2$, ammonia, etc.) through stoichiometry. When this system of equations is written into an algorithm, the computer can generate graphs of the accumulation of each species with respect to time. This is a valuable tool for generating a hard-copy 'fingerprint' of each fermentation batch process.

Test Fermentation vs. the Model

During the test fermentation, the $CO_2$ production rate was read every time a dry weight was taken. This 'grab sample' of $CO_2$ flow is not conducive to getting an accurate $CO_2$ production volume. As the fermentation progresses, $CO_2$ evolution waxes and wanes, presumably in response to the consumption of different substrates. The accuracy of the models predictions of the correlation between $CO_2$ volume produced and percentage sugar consumed will have to be assessed when an accurate $CO_2$ volume measurement is available (i.e. the prototype of the device incorporating this system). That said, it is interesting to look at the models predictions vs the experimental results. This comparison is contained in the evaluation of the test fermentation table. See FIG. 17

Figure 17:
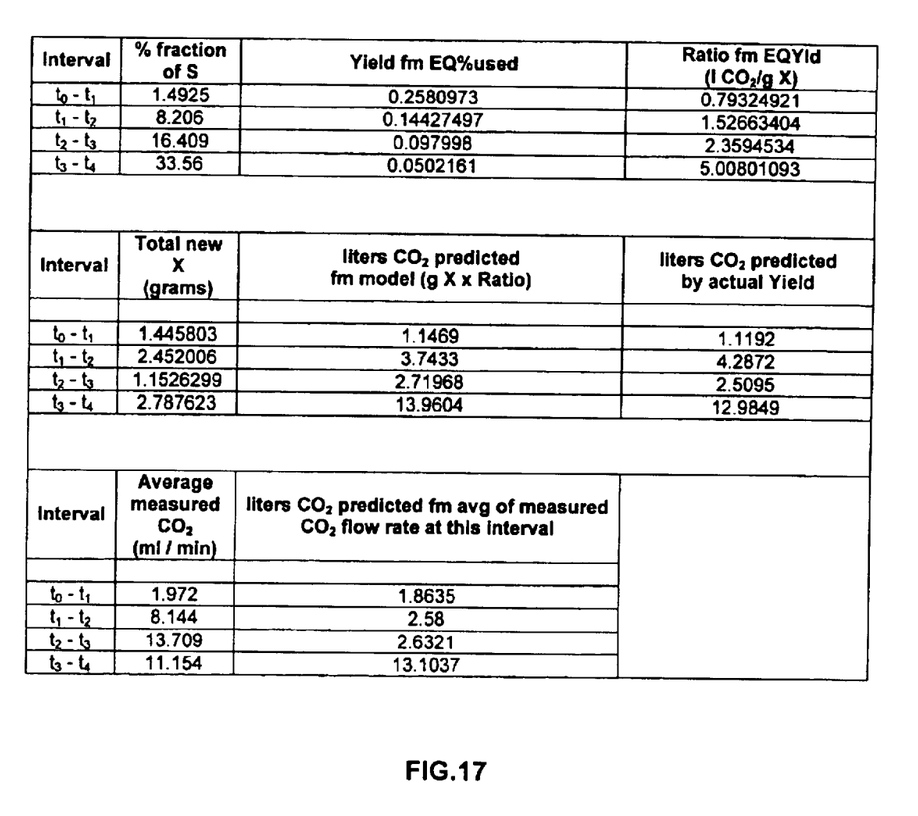
FIG. 17: This table compares the actual data to the results that would have been predicted by the model. The evaluation demonstrates that this technique is a valuable tool for the monitoring and control of fermentations.

A tighter correlation is needed between the yield curve and the actual yields. As you can see, the $t_1$–$t_2$ and $t_3$–$t_4$ intervals are off by the most with regard to the model vs stoichiometric $CO_2$ volume. Interval $t_1$–$t_2$ is somewhat of an outlier as can be seen on the graph, and the $t_3$–$t_4$ interval time is so long as to be problematic. The first interval ($t_0$–$t_0$) is long, and yet little substrate was consumed. The yeast probably spent quite a long time in lag phase during this interval. This initial zero $CO_2$ production was weighted equally with the $t_1$ flow rate of 3.972. That the zero should have been weighted more heavily accounts for the inflated liters $CO_2$ value (1.8635 l). This initial interval is expected to evolve a reduced amount of $CO_2$ because of its' solubility in water. The $CO_2$ only evolves after it passes its' solubility point. (See temperature vs $CO_2$ solubility curve).

The use of this model is intended not to use the model-derived $CO_2$/gramsxratio to compare the models $CO_2$ volume to others by multiplying out by the actual cell mass. This ratio is to be used the other way, by using the measured $CO_2$ volume to calculate the cell mass without ever actually taking dry weights. These values will be properly adjusted with regard to the endogenous decay rate. Accurate knowledge of the progression of the fermentation can be used to trigger temperature control programs. This not only allows the fermentation temperature control to be automated, but also enhances reproducibility.

Endogenous Decay and Normalization

Estimation of the endogenous decay rate (b) can be determined experimentally. A method I have used in the past is to grow up the yeast in a pure media (such as YM broth) so that there is a distinct and abrupt ending to its substrate consumption. Dry weights are then taken to observe the cell mass decrease as the cells consume themselves with time. This value is expected to decrease with decreasing temperature; another curve/correlation to refer to. I'm expecting a value of around 0.002/hour or so at room temperature (and going down with temperature from there).

If, when accurate $CO_2$ volumes are attained, the model still has discrepancies, a final 'data filter' or normalization curve can be used to help report the correct values. This final adjustment of 'fine tuning' will help us compensate for other subtle deficiencies (in the process or the calculations) that we are stuck with and need to correct. Some examples would be: 1) the evaporation of ethanol with the $CO_2$ will lower the ethanol yield, 2) organic acids produced at the start of the fermentation will make the $CO_2$ volumes observed lower the expected, etc.

What is claimed is:

1. A process of fermentation monitoring which quantifies reacting chemical species using a cellular yield curve to create a mass balance between all of the reacting chemical species, wherein the curve is a mathematical relationship between substrate utilization and cellular growth, and the fermentation monitoring process comprising the steps of:

(a) measuring starting chemical species concentrations;

(b) dynamically measuring one or all of the concentrations of the reacting chemical species;

(c) monitoring and describing the chemical species concentrations via a mass balance calculation as the fermentation proceeds.

2. A process of fermentation monitoring according to claim 1 using a flow-through or fed-batch system.

3. A process of fermentation control according to claim 1 comprising gauging the timing for control interventions and observing the effects of the intervention.

4. A process of fermentation monitoring according to claim 1 which comprises monitoring select fermentation substrates and products with the proviso that the monitoring and/or control methodology is the same.

5. A process of fermentation monitoring according to claim 1 which acquires empirical data to determine the chemical formula of the species in the reaction.

* * * * *